United States Patent
Wittenberger et al.

[11] Patent Number: 6,106,518
[45] Date of Patent: Aug. 22, 2000

[54] VARIABLE GEOMETRY TIP FOR A CRYOSURGICAL ABLATION DEVICE

[75] Inventors: Dan Wittenberger, Pierrefornds; Cristian Petre, Laval, both of Canada

[73] Assignee: Cryocath Technologies, Inc., St-Laurent, Canada

[21] Appl. No.: 09/057,899

[22] Filed: Apr. 9, 1998

[51] Int. Cl.$^7$ ................................................. A61B 17/36
[52] U.S. Cl. ............................... 606/23; 606/21; 607/96
[58] Field of Search ........................... 606/20–26; 607/96

[56] References Cited

U.S. PATENT DOCUMENTS

| | | |
|---|---|---|
| 3,791,387 | 2/1974 | Itoh . |
| 4,022,215 | 5/1977 | Benson . |
| 4,072,152 | 2/1978 | Linehan . |
| 4,699,147 | 10/1987 | Chilson et al. ........................ 128/642 |
| 4,758,221 | 7/1988 | Jureidini ................................ 604/95 |
| 4,930,494 | 6/1990 | Takehana et al. . |
| 5,010,894 | 4/1991 | Edhag ................................... 128/785 |
| 5,228,442 | 7/1993 | Imran .................................... 128/642 |
| 5,255,679 | 10/1993 | Imran .................................... 128/642 |
| 5,293,869 | 3/1994 | Edwards et al. ..................... 128/642 |
| 5,327,889 | 7/1994 | Imran .................................... 128/642 |
| 5,345,936 | 9/1994 | Pomeranz et al. ................... 128/642 |
| 5,400,783 | 3/1995 | Pomeranz et al. ................... 128/642 |
| 5,405,671 | 4/1995 | Kamin et al. ........................ 428/69 |
| 5,465,717 | 11/1995 | Imran et al. ........................ 128/642 |
| 5,487,385 | 1/1996 | Avitall ................................... 128/642 |
| 5,549,661 | 8/1996 | Kordis et al. ........................ 607/99 |
| 5,582,609 | 12/1996 | Swanson et al. ................... 606/39 |
| 5,647,871 | 7/1997 | Levine et al. ....................... 606/45 |
| 5,653,683 | 8/1997 | D'Andrea ........................... 604/21 |
| 5,680,860 | 10/1997 | Imran . |
| 5,694,646 | 12/1997 | Roberts ............................... 2/114 |
| 5,702,438 | 12/1997 | Avitall ................................. 607/122 |
| 5,730,704 | 3/1998 | Avitall ................................. 600/374 |
| 5,733,280 | 3/1998 | Avitall ................................. 606/23 |
| 5,738,683 | 4/1998 | Osypka ............................... 606/47 |
| 5,800,482 | 9/1998 | Pomeranz et al. ................. 607/101 |
| 5,846,238 | 12/1998 | Jackson et al. ..................... 606/41 |
| 5,868,735 | 2/1999 | Lafontaine ......................... 606/21 |
| 5,957,963 | 9/1999 | Dobak, III .......................... 607/104 |

FOREIGN PATENT DOCUMENTS

| | | |
|---|---|---|
| 0624347 | 11/1994 | European Pat. Off. . |
| 2655836 | 6/1991 | France . |
| 9804221 | 2/1998 | WIPO . |

*Primary Examiner*—Linda C. M. Dvorak
*Assistant Examiner*—Roy Gibson
*Attorney, Agent, or Firm*—Gunster, Yoakley, Valdes-Fauli & Stewart, P.A.

[57] ABSTRACT

A medical device includes a flexible member having a variable geometry tip with a thermally-transmissive region. A smooth fluid path is provided through the flexible member to and from the variable geometry, thermally-transmissive region. The thermally-transmissive region can be deformed.

30 Claims, 6 Drawing Sheets

VARIABLE GEOMETRY TIP FOR A CRYOSURGICAL ABLATION DEVICE

CROSS-REFERENCE TO RELATED APPLICATIONS

Not applicable.

STATEMENTS REGARDING FEDERALLY SPONSORED RESEARCH

Not applicable.

FIELD OF THE INVENTION

The invention relates to catheters, and more particularly to cryosurgical catheters used for tissue ablation.

BACKGROUND OF THE INVENTION

Many medical procedures are performed using minimally invasive surgical techniques, wherein one or more slender implements are inserted through one or more small incisions into a patient's body. With respect to ablation, the surgical implement can include a rigid or flexible structure having an ablation device at or near its distal end that is placed adjacent to the tissue to be ablated. Radio frequency energy, microwave energy, laser energy, extreme heat, and extreme cold can be provided by the ablation device to kill the tissue.

With respect to cardiac procedures, a cardiac arrhythmia can be treated through selective ablation of cardiac tissue to eliminate the source of the arrhythmia. A popular minimally invasive procedure, radio frequency (RF) catheter ablation, includes a preliminary step of conventional electrocardiographic mapping followed by the creation of one or more ablated regions (lesions) in the cardiac tissue using RF energy.

Deficiencies of radio frequency ablation devices and techniques have been overcome by using cryogenic techniques and devices for mapping and ablation, as taught in U.S. Pat. Nos. 5,423,807; and 5,281,213; and 5,281,215. However, even though combined cryogenic mapping and ablation devices permit greater certainty and less tissue damage than RF devices and techniques, both the cryogenic and the RF devices are configured for limited lesion spot sizes. In addition, these conventional devices are not well suited for tissue ablation for varying surface textures.

It would be desirable to have a catheter which overcomes the deficiencies of the prior art and which provides a lesion of variable length, even over non-uniform or irregular tissue surfaces.

BRIEF SUMMARY OF THE INVENTION

The present invention provides a cryogenic ablation system including a cryosurgical catheter with a variable geometry tip that is particularly well suited for creating varying size lesions on non-uniform tissue surface areas. In an exemplary embodiment, a cryogenic catheter includes a flexible member having a looped, thermally-transmissive region and a cryogenic fluid path through the flexible member to the looped, thermally-transmissive region. The looped, thermally-transmissive region can be deformable from an initial contact size through a variable range of contact sizes to create lesions of varying sizes and on varying surfaces. In one embodiment, the looped, thermally-transmissive region is defined by a helical coil can be at least partially embedded in the flexible member.

The cryogenic catheter of the invention can be a component in a cryogenic system that further includes a cryogenic fluid supply in communication with the cryogenic catheter, and a fluid controller interposed between the cryogenic catheter and the cryogenic fluid supply for regulating the flow of the cryogenic fluid into the cryogenic catheter. The cryogenic fluid can be a gas or a liquid.

BRIEF DESCRIPTION OF THE DRAWINGS

A more complete understanding of the present invention and the attendant advantages and features thereof will be more readily understood by reference to the following detailed description, when considered in conjunction with the accompanying drawings, wherein:

FIG. 3b illustrates a sample deformation of the looped tip region of the catheter of FIG. 3a;

DETAILED DESCRIPTION OF THE INVENTION

Figure 1:
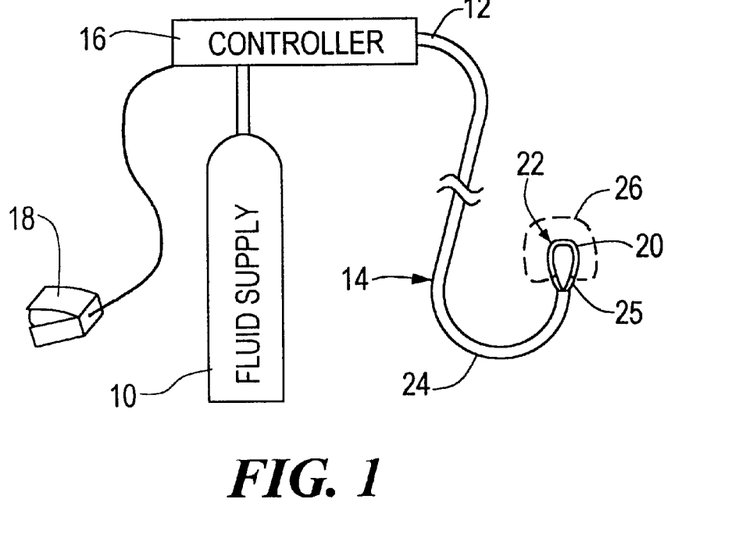
FIG. 1 is a schematic illustration of an embodiment of a cryosurgical system in accordance with the invention.

FIG. 1 is a schematic illustration of a cryosurgical system utilizing a cryogenic cooling structure in accordance with the teachings of the present invention. The system includes a supply of cryogenic or cooling fluid 10 in communication with the proximal end 12 of a catheter 14 having a variable geometry tip. A fluid controller 16 is interposed or in-line between the cryogenic fluid supply 10 and the catheter 14 for regulating the flow of cryogenic fluid into the catheter in response to a controller command. Controller commands can include programmed instructions, sensor signals, and manual user input. For example, the fluid controller 16 can be programmed or configured to increase and decrease the pressure of the fluid by predetermined pressure increments over predetermined time intervals.

In another exemplary embodiment, the fluid controller 16 can be responsive to input from a foot pedal 18 to permit flow of the cryogenic fluid into the catheter 14. One or more temperature sensors 20 in electrical communication with the controller 16 can be provided to regulate or terminate the flow of cryogenic fluid into the catheter 14 when a predetermined temperature at a selected point or points on or within the catheter is/are obtained. For example, a temperature sensor can be placed at the midpoint of the loop while other temperature sensors can be located at spaced intervals on the loop.

The cryogenic fluid can be in a liquid or a gas state. An extremely low temperature can be achieved within the loop, and more particularly on the surface of the catheter by cooling the fluid to a predetermined temperature prior to its introduction into the catheter, by allowing a liquid state cryogenic fluid to boil or vaporize, or by allowing a gas state cryogenic fluid to expand.

Exemplary liquids include chlorodifluoromethane, polydimethylsiloxane, ethyl alcohol, HFC's such as AZ-20 (a 50—50 mixture of difluoromethane & pentafluoroethane sold by Allied Signal), and CFC's such as DuPont's Freon. Exemplary gasses include nitrous oxide and carbon dioxide.

Referring generally to FIGS. 1–4, in an exemplary embodiment, the catheter 14 includes a flexible guiding sheath 24, a flexible member 25 having a looped, thermally-transmissive region 26 with a fluid path through the flexible member 25 to the thermally-transmissive region 26. A fluid path is also provided from the thermally-transmissive region 26 to a point external to the catheter, such as the proximal end 12. Although described in greater detail below, exemplary fluid paths can be one or more channels defined by the flexible member 25, and/or by one or more additional flexible tubes that are internal to the flexible member 25. Also, even though many materials and structures can be thermally conductive or thermally transmissive if chilled to a very low temperature and/or cold soaked, as used herein, a "thermally-transmissive region" is intended to broadly encompass any structure or region of the catheter 14 that readily conducts heat.

For example, a metal structure exposed (directly or indirectly) to the cryogenic fluid path is considered a thermally-transmissive region 26 even if an adjacent polymeric or latex catheter portion also permits heat transfer, but to a much lesser extent than the metal. Thus, the thermally-transmissive region 26 can be viewed as a relative term to compare the heat transfer characteristics of different catheter regions or structures. A thermally-transmissive region or element is not intended to encompass a structure that is excited by RF or other energy source to a point where it begins to radiate heat, for example.

Furthermore, while the looped, thermally-transmissive region 26 can include a single, continuous, and uninterrupted surface or structure, it can also include multiple, discrete, thermally-transmissive structures that collectively define the looped, thermally-transmissive region. Depending on the ability of the cryogenic system, or portions thereof, to handle given thermal loads, the ablation of varying size and/or non-uniform tissue surfaces can be performed in a single or multiple cycle process without having to relocate the catheter one or more times or drag it across tissue. Additional details of the looped, thermally-transmissive region 26 and the thermal transfer process are described in greater detail below.

Figure 2:
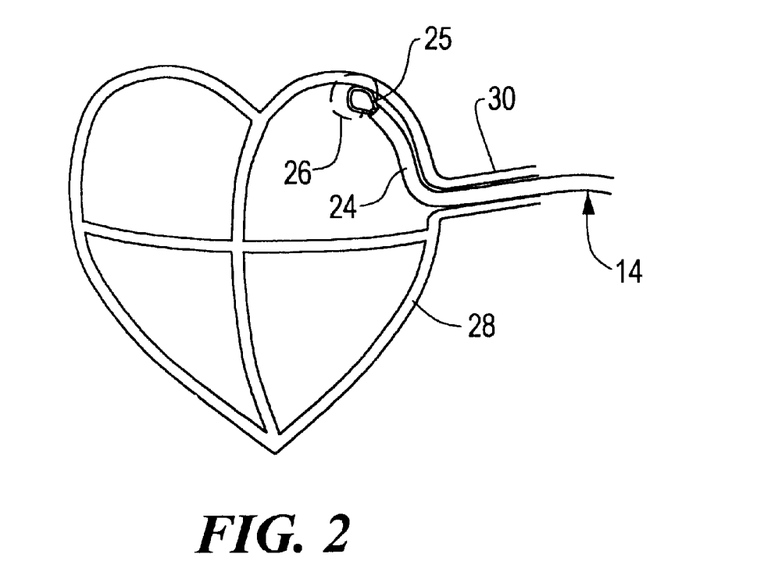
FIG. 2 is a sectional view of a heart muscle showing placement of the catheter of FIG. 1.

The cryogenic system of FIG. 1 is better understood with reference to its use in an operative procedure as shown in FIG. 2. Following the determination of a proposed lesion site within a heart muscle 28 for example, the catheter 14 is directed through a blood vessel 30 to a region within the heart, such as an auricle, where the lesion will be made. The looped, thermally-transmissive region 26 is placed proximate to the tissue to be ablated. The looped, thermally-transmissive region 26 of the catheter may be deformed to conform to the curvature of the tissue before, during, or after placement against the tissue. The controller 16 allows or causes cryogenic fluid to flow from the cryogenic fluid supply 10 to the fluid path in the catheter 14 and thence to the looped, thermally-transmissive region 26 to ablate the desired area or to cold map along the same tissue area.

Figure 3A:
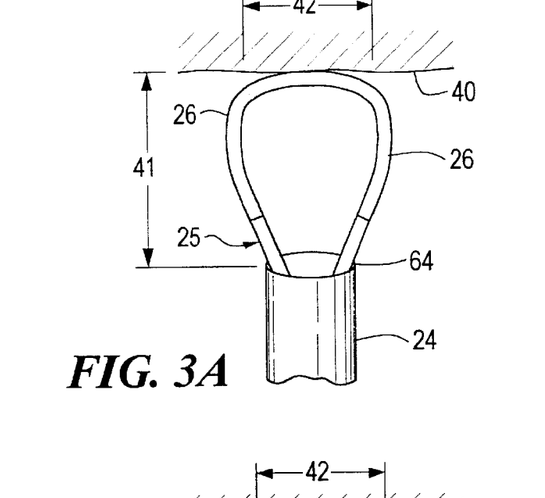
FIG. 3a illustrates the looped tip region of one embodiment of the catheter in accordance with the invention.
Figure 3B:
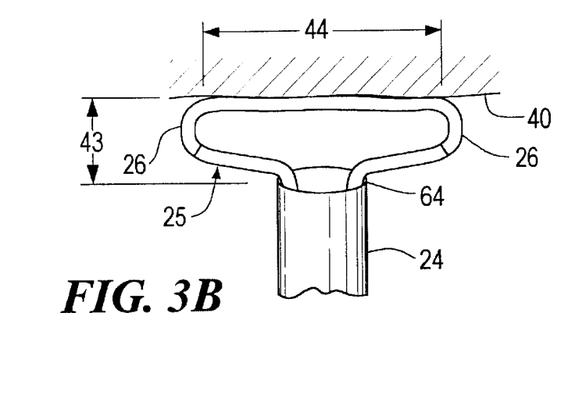

In exemplary embodiments of the invention, the looped, thermally-transmissive region 26 of the catheter 14 is actively deformable. As more clearly shown in FIGS. 3a and 3b, by changing the initial position of a distal end 64 of the guiding sheath 24 relative to the tissue 40, in conjunction with varying the pressure applied on the loop by the operator, the contact lengths 42 and 44 between the thermally transmissive region 26 and the tissue 40 can be modified and controlled. In FIG. 3a, the thermally transmissive region 26 contacts tissue 40 along contact length 42. As the distal end 64 of the guiding sheath 24 moves closer to tissue 40, the thermally transmissive region 26 deforms to contact length 44, shown in FIG. 3b. As shown in FIGS. 3a and 3b, the guiding sheath varies from an initial distance 41 to a final distance 43, relative to the tissue 40, thereby forcing a deformation of the looped, thermally transmissive region 26. Varying the sheath position and pressure allows the creation of ablation areas of different lengths and improves contact even when non-uniform surfaces such as ridges or bumps are encountered, as more clearly shown in FIG. 5.

Figure 4A:
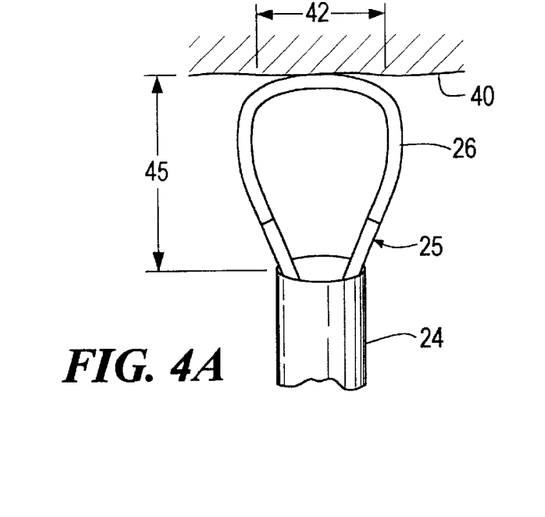
FIG. 4a illustrates the looped tip region of one embodiment before extension of the flexible member of the catheter in accordance with the invention.
Figure 4B:
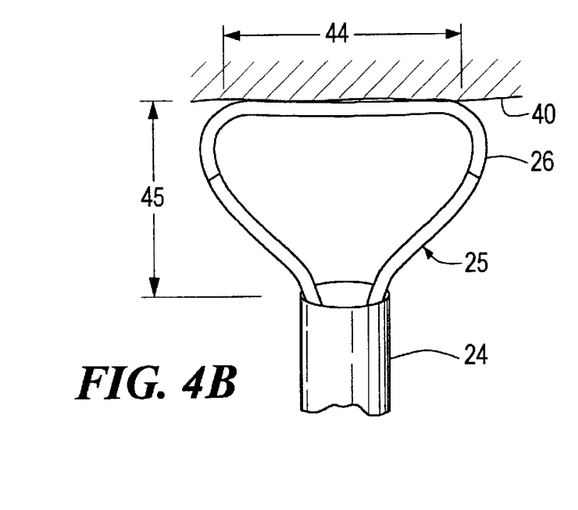
FIG. 4b illustrates the looped tip region of one embodiment after extension of the flexible member of the catheter in accordance with the invention.

Alternatively, as shown in FIGS. 4a and 4b, a greater length of the flexible member 25 can be extended from the distal end 64 without moving the guiding sheath 24 relative to the tissue 40 to create variations in the size of the ablation contact areas. As shown in FIG. 4a, the guiding sheath 24 is at an initial distance 45 from the tissue area 40. As more of the flexible element 25 is exposed, as shown in FIG. 4b, the distance of the guiding sheath 24 remains at a constant distance 45 relative to the tissue 40. However, the contact area 44 increases due to the greater length of the flexible element 25 exposed, thereby increasing the contact area 44 of the looped, thermally transmissive regions 26 with the tissue 40. By either varying the sheath position, the extension of the flexible member and/or the pressure placed upon the flexible member, the catheter 14 may be actively deformed by the user. In other cases, a reactive or passive deformation of the thermally transmissive region of the catheter is desirable as described below.

Figure 5:
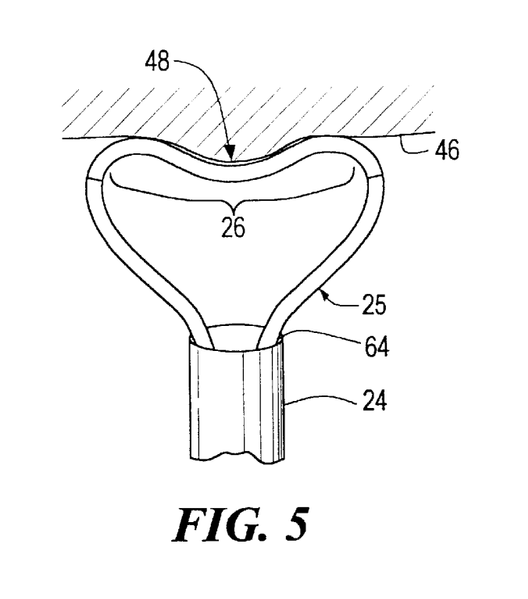
FIG. 5 illustrates the application of the catheter for non-uniform surface lesions.

As shown in FIG. 5, the thermally transmissive region 26 of the flexible member 25 conforms to the contour of tissue surface 46 which includes a raised ridge 48. In contrast, if the ablation structure was rigid, a raised ridge 48 or other surface irregularity might prevent some or most of the rigid ablation structure from contacting the targeted tissue area. Accordingly, when in contact with irregular or uneven surfaces, the thermally transmissive region 26 of the flexible member 25 will undergo a reactive deformation to conform to the irregular or uneven surface. It is also contemplated that the reactive deformation of the flexible member can be combined or supplemented with some active deformation on the part of an operator of the device, depending on the amount of tissue area required to be ablated.

Figure 6:
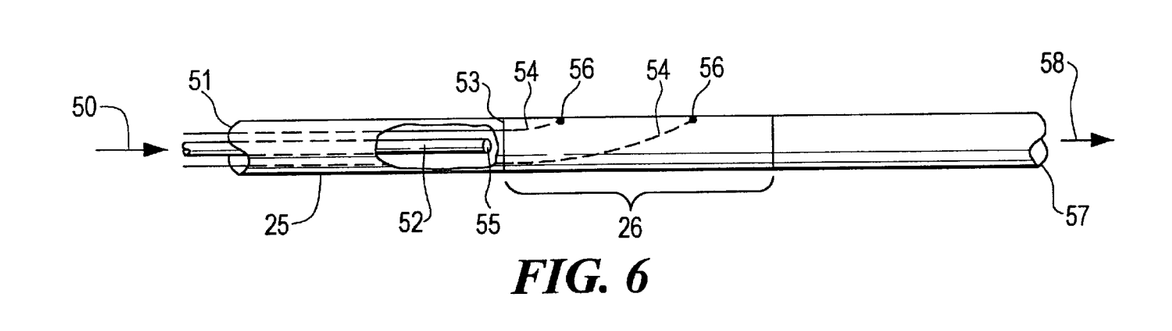
FIG. 6 illustrates the internal construction of one embodiment of the catheter in accordance with the invention.

The internal construction of the looped, thermally-transmissive region 26 will now be described in greater detailed with reference to FIG. 6 which, for clarity, shows the normally looped, thermally-transmissive region 26 in an elongated fashion. As shown in FIG. 6, an injection tube 52 is disposed within the flexible member 25. In this embodiment, the construction and structure of the flexible member 25 uses a thin, e.g. approximately 0.00035" to 0.0015" thick, outer jacket made of a polymer or similar material as is known to those skilled in the art. The outer diameter of the flexible member can be in the range of 0.040" to 0.118". It is contemplated that except for the thermally-transmissive region 26, a thicker outer jacket may also be used. In another embodiment, the injection tube itself, not shown, may serve as the looped, thermally transmissive region without being enclosed within an external flexible member.

Again, as shown in FIG. 6, a distal end 55 of the injection tube 52 is placed proximate to the beginning area 53 of the thermally-transmissive region 26. One or more thermocouples 56 also are placed in the thermally-transmissive region 26. The thermocouple wires 54 as well as all the other wires (ECG, for example) are guided through the flexible member 25 through its proximal end 51, thus leaving the thermally-transmissive region more exposed to the vacuum applied at the distal end 57. The velocity vectors, as respectively designated by arrows 50 and 58, of the liquid and the vapor have the same direction, e.g. from the proximal end 51 towards the distal end 57. Accordingly, the construction described above provides for a smooth flow path of the liquid and vapor from the proximal end 51 to the distal end 57 thereby overcoming the deficiencies typical of closed end type elongate catheters.

Figure 7:
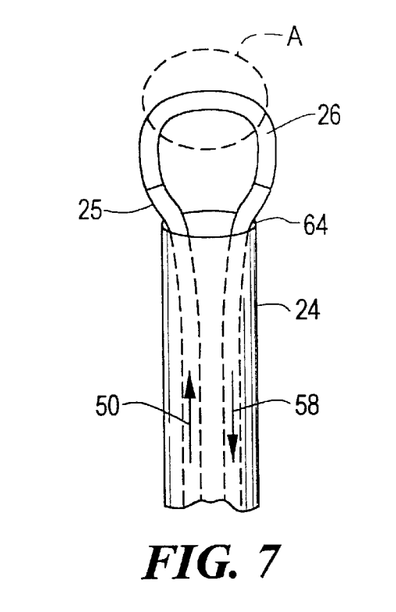
FIG. 7 illustrates the flow path within the catheter of FIG. 3.

Referring to FIG. 7, the catheter assembly described in FIG. 6 is bent and folded over in a loop-like manner and passed through the guiding sheath 24. The resultant looped, thermally-transmissive region 26 is passed through and should then exit the guiding sheath 24 at its distal end 64. A portion of the flexible member 25 extending beyond the boundaries of the looped, thermally-transmissive region 26 can also protrude from the distal end 64. It is contemplated that a wall portion of the flexible guiding sheath 24 can include a metal braid to make the catheter torqueable for overall catheter steering and placement. Additionally, a cord, wire or cable can be incorporated with, or inserted into, the guiding sheath 24 for deformation of the guiding sheath during an operative procedure.

Figure 8:
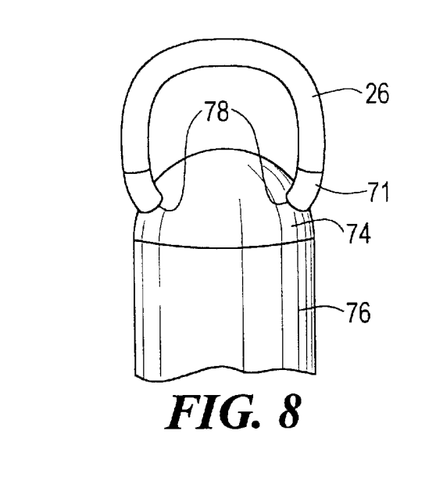
FIG. 8 illustrates yet another embodiment of the catheter.

In another embodiment of the catheter as shown in FIG. 8, an end cap 74 may be used to predefine the plane in which the looped, thermally-transmissive region 26 will evolve. In this embodiment, a guiding sheath 76 terminates at its distal end with the end cap 74. The end cap 74 may be integrally formed with the guiding sheath 76 or it may be a separate piece which is independently attached to the guiding sheath 76. In one exemplary embodiment, the end cap 74 has a pair of openings 78 which are situated on the end cap 74 and spaced apart at a predetermined distance relative to one another. The openings 78 are sized to accept the flexible catheter member 71. Accordingly, the deformation of the catheter member 71 is defined by the location of the openings 78. It is contemplated that any number of holes corresponding to the number of thermally-transmissive loops being used can be disposed on the end cap 74.

Having described the function of the cryogenic catheter 14 and its use in a system context, several exemplary embodiments of the thermally transmissive region 26 of the catheter are now described in greater detail.

Figures 9, 10, 11, 12, 13, 14, 15:
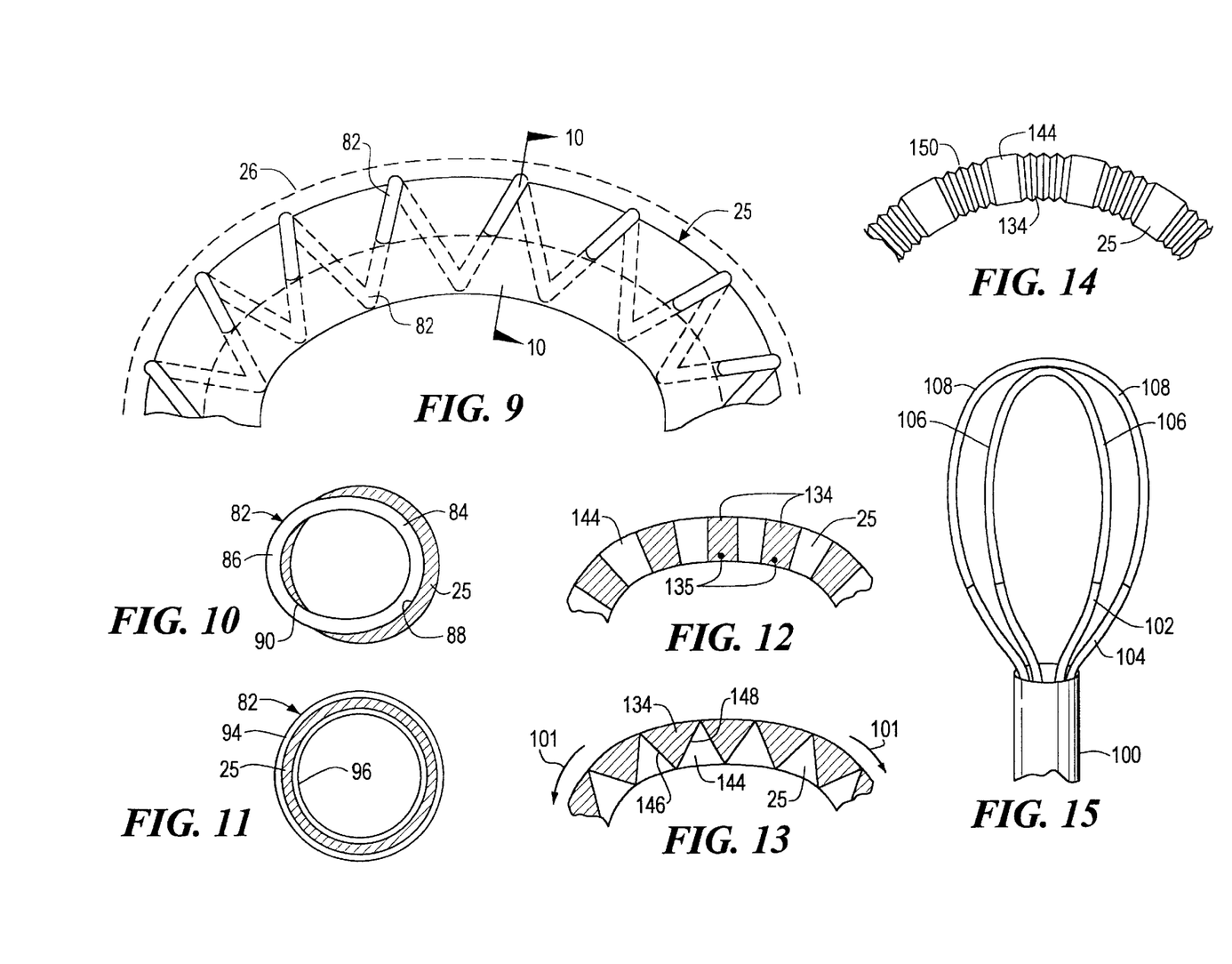
FIG. 9 illustrates a helical coil thermally-transmissive element used in conjunction with the catheter in accordance with the invention.
FIG. 10 is a sectional view of the catheter of FIG. 9 taken along line 10—10.
FIG. 11 is a sectional view of an alternative embodiment of the catheter illustrated in FIG. 9.
FIG. 12 is a detailed view of yet another embodiment of portion A shown in FIG. 7.
FIG. 13 is a detailed view of yet another embodiment of portion A shown in FIG. 7.
FIG. 14 is a detailed view of yet another embodiment of portion A shown in FIG. 7.
FIG. 15 illustrates yet another embodiment of the catheter.

Referring now to FIG. 9, an exemplary approach is shown for providing multiple thermally-transmissive segments in a spaced-apart relationship. FIG. 9 illustrates a catheter embodiment having a looped, thermally-transmissive region 26 that includes a helical coil 82 that can be at least partially embedded in the flexible member 25. As shown more clearly in FIG. 10, at least a first portion 84 of the helical coil 82 is exposed to a fluid path within the flexible member 25 and a second portion 86 of the helical coil is exposed to the exterior of the flexible member. As described above with respect to FIG. 10, the first portion 84 of the coil can be substantially flush with, recessed below, or protruding from an inner surface 88 of the flexible member 25. Similarly, the second portion 86 of the coil 82 can be substantially flush with, recessed below, or protruding from an outer surface 90 of the flexible member 25.

Referring to FIG. 11, an alternative embodiment is shown wherein a first portion 82 of the coil 94 is exposed around the entire circumference of the flexible member 25, and a second portion 96 is exposed to a fluid path around the inner surface of the flexible member 25. In addition, while the coil as shown and described herein is solid, in other embodiments the coil can be an elongate, hollow, gas expansion chamber.

Referring now to the embodiment depicted in FIG. 12, multiple thermally-transmissive elements 134 are integral with the flexible member 25 forming the looped, thermally-transmissive region 26 of the catheter. Any or all of the thermally-transmissive elements 134 can be substantially flush with, recessed below, or protruding from a portion of the flexible member 25. The thermally-transmissive elements 134 are separated by flexible portions of material 144 than can range from slightly less thermally-transmissive than the adjacent thermally-transmissive elements to substantially less thermally-transmissive than the adjacent elements. In the illustrated embodiment of FIG. 12, the thermally-transmissive elements 134 are annular, cylindrical elements which are made of gold-plated copper, bronze or any other bio-compatible metal or alloy. Thermocouples 135 can be associated with one or more of the elements 134. The thermally-transmissive elements 134 can be completely exposed, embedded, or a combination thereof along the full 360° of the catheter's circumference. In certain applications the thermally-transmissive elements traverse or define less than 360° of the catheter's circumference. The longitudinal width of each thermally-transmissive element 134, the spacing between elements, the material thickness, and the material composition are matched with a selected cooling fluid and fluid delivery pressure to produce the desired lesion.

The embodiment illustrated in FIG. 13 is substantially identical to the embodiment of FIG. 12, however, at least one of the thermally-transmissive elements 134 includes a first open end 146 that defines a first plane and a second open end 148 that defines a second plane, wherein the first and second planes intersect to give the annular elements a wedge-like appearance. Such a configuration permits adjacent thermally-transmissive elements 134 to be positioned very closely together, but it can limit the possibilities for deforming the thermally-transmissive region 26, which, in this embodiment, is flexible in the direction indicated by the arrows 101.

With respect to the embodiments shown in both FIGS. 12 and 13, the thermally-transmissive elements 134 are substantially rigid and are separated and/or joined by a flexible bio-compatible material 144. However, in other embodiments the thermally-transmissive elements 134 are flexible and are interdigitated with either rigid or flexible segments. FIG. 14, for example, illustrates an embodiment of the cryogenic catheter having a plurality of thermally-transmissive elements 134 that are flexible. The flexibility is provided by a folded or bellows-like structure 150. In addition to being shapable, a metal bellows can have enough stiffness to retain a selected shape after a deforming or bending step.

In other embodiments, not shown, the catheter or thermally-transmissive loop itself is constructed of a polymer or elastomer which is thin enough to permit thermal transfer. For, example, polyamide, PET or PTFE would be suitable to provide such thermal transfer.

Referring to FIG. 15, a further embodiment is shown having a pair of looped, thermally-transmissive regions. The embodiment shown in FIG. 15 includes a guiding sheath 100, a first flexible member 102 forming a first looped, thermally-transmissive region 106, and a second flexible member 104 forming a second looped, thermally-transmissive region 108. The first and second flexible members 102 and 104 may be situated in an overlapped orientation as shown or the members may also be arranged adjacent to one another.

Figure 16:
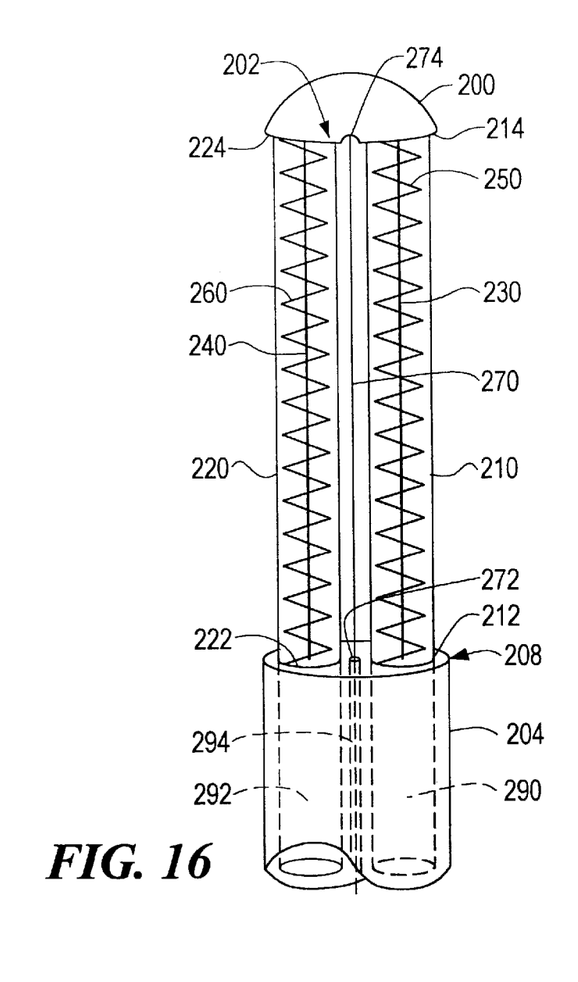
FIG. 16 illustrates yet another embodiment of the catheter.
Figure 17:
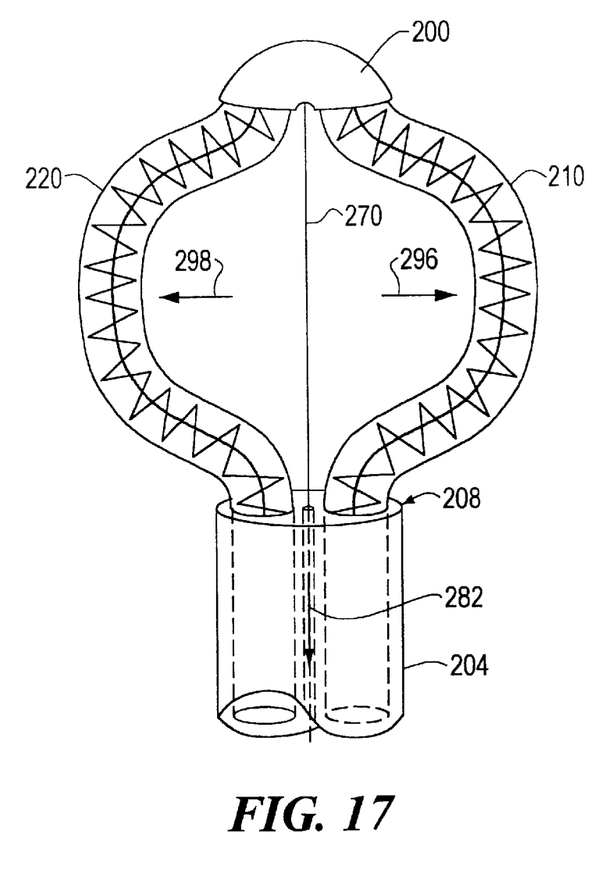
FIG. 17 illustrates the embodiment of FIG. 16 in an expanded condition.

Referring to FIGS. 16 and 17, a further embodiment is shown having means to control the deformation of the thermally-transmissive region. As shown in an unexpanded condition in FIG. 16, this embodiment includes an end cap 200, two substantially parallel flexible members 210 and 220, a sheath 204 and means for controlling deformation of the flexible members, which consists of a pull wire 270.

The flexible members 210 and 220 and the pull wire 270 are disposed within lumens in the sheath 204 at one end and are disposed a distance within openings, not shown, in the end cap 200 at the other end.

As shown in FIG. 16, the sheath 204 contains a first lumen 290, a second lumen 292 and a third lumen 294. At least a portion of the first flexible member 210 at a proximal end 212 is disposed within the first lumen 290. Similarly, at least a portion of the second flexible member 220 at a proximal end 222 is disposed within the second lumen 292. Within the first flexible member 210 is disposed a first resilient member 230 and a first coil 250. Within the second flexible member 220 is disposed a second resilient member 240 and a second coil 260. The resilient members and coils extend from the proximal to the distal ends of the flexible members. The resilient members provide axial support for the flexible members while the coils provide radial or lateral support of the flexible members.

The end cap 200 is attached at an inferior surface 202 to distal ends 214 and 224 of the first and second flexible members 210 and 220, respectively. Also attached to the inferior surface 202 of the end cap 200 is a distal end 274 of the pull wire 270. The pull wire 270 at a proximal end 272 is disposed within the third lumen 294 of the sheath 204. The third lumen 294 is centrally disposed within the sheath 204 relative to the first and second lumens 290 and 292.

Figure 18:
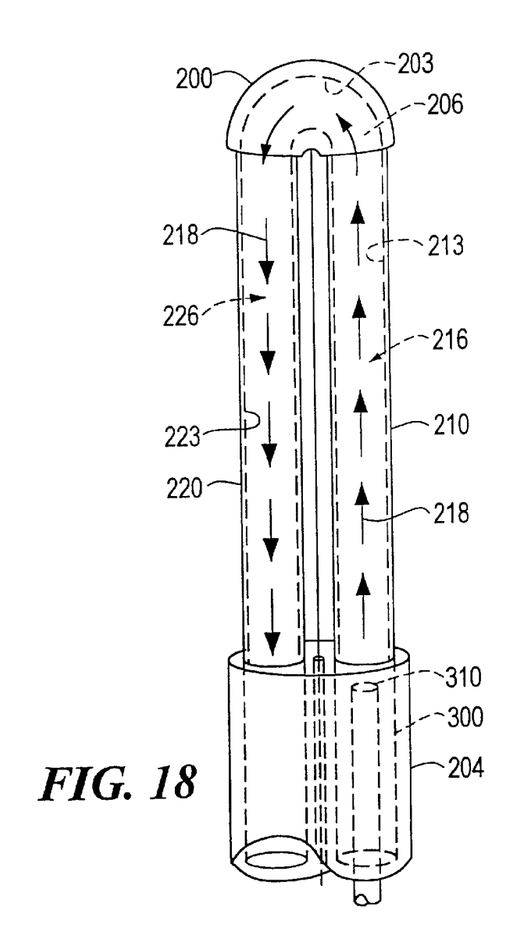
FIG. 18 illustrates the flow path for the embodiment of FIG. 16.

A portion of the pull wire 270 may extend a distance within the inferior surface 202 of the end cap 200 to prevent the pull wire 270 from unintentionally detaching from the end cap 200. In an exemplary embodiment, the end cap 200 has an inner lumen 206, as shown in FIG. 18, extending therethrough to provide for adequate expansion of the cryogenic fluid, if required. The end cap may be electrically conductive for use as an ECG probe and is constructed of a medical grade material such as platinum, iridium, platinum-iridium alloy, gold or other material as is known to those skilled in the art.

The embodiment of FIG. 16 is shown in FIG. 17 in a deformed condition. By placing tension on the pull wire 270, in the direction shown by arrow 282, the end cap 200 is brought towards a distal end 208 of the sheath 204. As the end cap 200 moves towards the distal end 208 of the sheath 204, the flexible members 210 and 220 deform in the direction of arrows 296 and 298. The coils 250 and 260 in conjunction with resilient members 230 and 240 provide the device with consistent deformation control within the flexible members 210 and 220. Accordingly, the degree of deformation can be controlled by varying the stiffness of the coils and resilient members within the flexible members. The coils and resilient members may be constructed of spring tempered steel, aluminum, plastic, rubber or other materials which have the desired supporting characteristics. In other embodiments, a shape memory alloy or superelastic alloy such as Nitinol® may be used for the construction of the coils and resilient members.

The pull wire 270 may be tensioned to deform the device. In an exemplary embodiment, the pull wire 270 is tensioned by the operator depending upon the specific application site. By gradually placing more tension upon the pull wire 270, the end cap 200 will be brought closer and closer to the distal end 208 of the sheath 204, resulting in deformation of the thermally transmissive region. In an exemplary embodiment, the pull wire 270 is constructed of steel but may also be constructed of other similar materials.

An exemplary flow path of the embodiment shown in FIGS. 16 and 17 is shown in FIG. 18. The flexible member 210 includes an inner surface 213 which defines an inner lumen or passageway 216. Likewise, flexible member 220 includes an inner surface 223 which defines an inner lumen or passageway 226. Interposed between the flexible members is the end cap 200 with inner surface 203 which defines the connecting lumen or passageway 206. The interconnected passageways thereby define a smooth flow path within the thermally transmissive region.

Disposed within the flexible member 210 is an apertured tube 300 which provides an injection of cryogenic fluid from a distal end 310 into the passageway 216. An exemplary flow path for the cryogenic fluid is designated by arrows 218. As shown, the fluid path begins at a point proximal the proximal end 212 of the flexible member 210 and is exhausted at a point proximal the proximal end 222 of the flexible member 220. A vacuum is used to lower the boiling point of the cryogenic liquid or to improve the cooling of the thermally transmissive region if gas expansion is used. In other embodiments, the flow path may be reversed with the entry and exit points switched.

Figure 19:
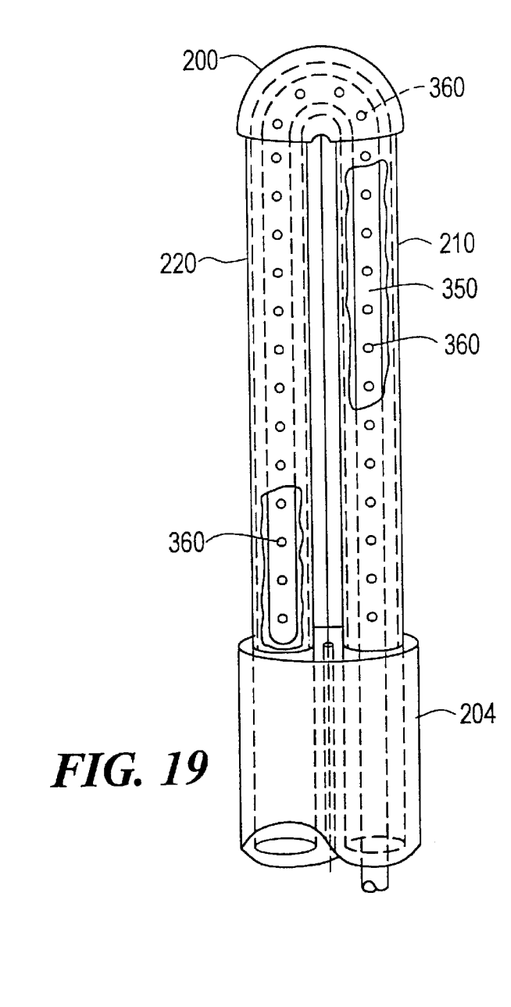
FIG. 19 illustrates another embodiment of an injection tube for use with the present invention.

In a further embodiment, a multi-port injection tube 350, as shown in FIG. 19, is used instead of a single apertured tube as illustrated in FIG. 18. In an exemplary configuration, the multi-port injection tube 350 is disposed along the entire length of the smooth flow path within the interconnected passageways of the thermally transmissive region. Disposed along the multi-port injection tube 350 are a plurality of apertures 360 which can provide multiple simultaneous injections of cryogenic fluid. The benefits of the multi-port injection tube include increased control and dispersion of the cryogenic fluid in the thermally transmissive region which allows for a more uniform phase change in the case of an injected fluid.

Accordingly, the present invention solves many prior art problems encountered when attempting to utilize flexible type catheters to adapt to varying size and surface conditions. For example, for cryogenic catheters with very small dimensions, the vacuum path becomes too restrictive and the phase change does not take place in optimum conditions (higher temperatures). A restricted vacuum path also leads to pressure build-up at the tip of the catheter. Furthermore, in conventional catheter construction, numerous electrical wires as well as the cryogenic injection tube itself also take up part of the available section of the vacuum path, thereby further restricting the vacuum path. In contrast, the present invention utilizes a smooth flow path, as clearly illustrated in FIGS. 6, 7, and 18.

A variety of modifications and variations of the present invention are possible in light of the above teachings. Specifically, any number of flexible members forming a plurality of looped, thermally-transmissive regions may be used although the embodiments shown utilize a singular and a double looped element. In addition, although many embodiments are illustrated that are adapted for insertion into the vascular system and are therefore slender and flexible, other embodiments may be thick and rigid, and introduced into the body directly through incisions or through structures such as trocars. Furthermore, although some of the illustrated devices are particularly well suited for cardiac procedures, the same embodiments and others are equally suited to other organs and/or any body portion that would benefit from the application of thermal energy. Thus, the devices as shown are not to be limited to catheters or to use within the vascular system, but should be viewed more broadly as cryogenic structures or portions thereof. It is therefore understood that, within the scope of the appended claims, the present invention may be practiced otherwise than as specifically described hereinabove. All references cited herein are expressly incorporated by reference in their entirety.

What is claimed is:

1. A medical device comprising:
   a cooling structure having a thermally-transmissive region configured for contacting and cryoablating tissue, wherein at least a portion of the thermally-transmissive region is flexibly deformable to controllably vary an area of tissue contact of said region, and wherein the thermally-transmissive region is a flexible loop.

2. A medical device comprising:
   a cooling structure having a thermally-transmissive region, wherein at least a portion of the thermally-transmissive region is deformable, wherein the thermally-transmissive region is a flexible loop, and wherein the thermally-transmissive region includes a helical coil.

3. A medical device comprising:
   a cooling structure having a thermally-transmissive region, wherein at least a portion of the thermally-transmissive region is deformable, wherein the thermally-transmissive region is a flexible loop, and wherein the thermally-transmissive region includes a plurality of thermally-transmissive elements joined in a spaced-apart relationship by flexible connecting elements.

4. A medical device comprising:
   a cooling structure having a thermally-transmissive region configured for contacting and cryoablating tissue, wherein at least a portion of the thermally-transmissive region is flexibly deformable to controllably vary an area of tissue contact of said region, and wherein the thermally-transmissive region comprises a plurality of flexible loops.

5. A cooling structure for a medical device comprising:
   a catheter having a flexible member having a looped thermally-transmissive region configured for contact cooling of tissue; and
   a fluid path through the looped, thermally-transmissive region providing fluid to cool said thermally-transmissive region, and wherein said flexible member flexes to controllably define an area of tissue contact in said thermally-transmissive region.

6. The cooling structure of claim 5, further comprising:
   a second flexible member having a second looped, thermally-transmissive region; and
   a second fluid path through the second looped, thermally-transmissive region.

7. The cooling structure of claim 5, wherein the looped, thermally-transmissive region includes a thermally-transmissive flexible material.

8. The cooling structure of claim 5, further comprising a guiding sheath that envelops a portion of the flexible member.

9. The cooling structure of claim 8, wherein the guiding sheath has a proximal and a distal end, and wherein the flexible member is movable with respect to the guiding sheath.

10. A cooling structure for a medical device comprising:
    a flexible member having a looped thermally-transmissive region; and
    a fluid path through the looped, thermally-transmissive region, wherein the looped, thermally-transmissive region includes a helical coil.

11. A cooling structure for a medical device comprising:
    a flexible member having a looped thermally-transmissive region; and
    a fluid path through the looped, thermally-transmissive region, wherein the thermally-transmissive region includes a plurality of thermally-transmissive elements joined in a spaced-apart relationship by flexible connecting elements.

12. The cooling structure of claim 11, wherein the flexible element deforms in response to contact with a body tissue to conform to the surface of the body tissue.

13. A cooling structure for a medical device comprising:
    a flexible member having a looped thermally-transmissive region;
    a fluid path through the looped, thermally-transmissive region,
    wherein the looped, thermally-transmissive region includes a thermally-transmissive flexible material selected from the group consisting of polyimide, PET, and PTFE.

14. A cooling structure for a medical device comprising:
    a flexible member having a looped thermally-transmissive region;
    a fluid path through the looped, thermally-transmissive region;

further comprising a guiding sheath that envelops a portion of the flexible member, wherein the guiding sheath has a proximal and a distal end, and wherein the flexible member is movable with respect to the guiding sheath and the looped, thermally-transmissive region is increased and decreased in size by moving the flexible member with respect to the guiding sheath.

15. A medical device comprising:

a sheath having a proximal end, a distal end, and a passage from the distal end to the proximal end; and a flexible member at least partially disposed within the passage of the sheath, the flexible member having a first end, a second end, and a thermally-transmissive region therebetween, wherein the flexible member defines a fluid path through the thermally-transmissive region, and wherein the flexible member is positioned within the passage so that the thermally-transmissive region forms a loop near the distal end of the sheath that flexes to define a region of cooling tissue contact, and the first and second ends of the flexible member extend from the proximal end of the sheath.

16. A medical device comprising:

a sheath having a proximal end, a distal end, and a passage from the distal end to the proximal end; and a flexible member at least partially disposed within the passage of the sheath, the flexible member having a first end, a second end, and a thermally-transmissive region therebetween, wherein the flexible member defines a fluid path through the thermally-transmissive region, and wherein the flexible member is positioned within the passage so that the thermally-transmissive region forms a loop near the distal end of the sheath and the first and second ends of the flexible member extend from the proximal end of the sheath further comprising a fluid injection tube disposed within the fluid path, wherein the fluid injection tube includes an outlet near the thermally-transmissive region.

17. A medical device comprising:

a first flexible member including an interior cooling fluid passage;

a second flexible member including an interior cooling fluid passage and oriented substantially parallel with the first flexible member;

an end cap, the end cap joining the first and second flexible members at distal ends thereof; and a pull wire secured to the end cap, whereby applying tension on the pull wire causes the first and second flexible members to deform from the substantially parallel orientation and to apply cooling contact to tissue.

18. The device of claim 17, further comprising a sheath, the sheath having a plurality of lumens formed therein whereby the first and second flexible members extend at least a portion within the lumens.

19. The device of claim 18, wherein at least a portion of the pull wire extends into one of the plurality of lumens in the sheath.

20. The device of claim 17, further comprising a plurality of coils disposed within the flexible members.

21. The device of claim 20, wherein the coils are constructed of a shape memory alloy.

22. The device of claim 20, wherein the coils are constructed of a super-elastic alloy.

23. The device of claim 17, further comprising a plurality of resilient members disposed within the flexible members.

24. The device of claim 23, wherein the resilient members are constructed of a shape memory alloy.

25. The device of claim 23, wherein the resilient members are constructed of a super-elastic alloy.

26. The device of claim 17, further comprising an internal lumen which defines a smooth flow path for expansion of a cryogenic fluid.

27. The device of claim 17, wherein the end cap is electrically conductive.

28. The device of claim 17, wherein the flexible members have inner lumens.

29. The device of claim 27, wherein the end cap has an inner lumen which interconnects the inner lumens of the flexible members thereby defining smooth flow path.

30. The device of claim 17, further comprising a multi-port injection tube disposed within the flexible members.

* * * * *